(12) United States Patent
Keyer et al.

(10) Patent No.: US 7,131,974 B2
(45) Date of Patent: Nov. 7, 2006

(54) SURGICAL DRILL GUIDE

(76) Inventors: Thomas R. Keyer, 338 Cashel Ct., Aston, PA (US) 19014; Roger Berger, St. Tantaleon Strasse 20, Büren (CH) 4413; Douglas S. Kephart, 1098 Smithbridge Rd., Glen Mills, PA (US) 19342-1206; Martin Walther, 153 Rue de General Segur, Thomery (FR) 77810

( * ) Notice: Subject to any disclaimer, the term of this patent is extended or adjusted under 35 U.S.C. 154(b) by 73 days.

(21) Appl. No.: 10/683,000

(22) Filed: Oct. 14, 2003

(65) Prior Publication Data
US 2005/0119663 A1    Jun. 2, 2005

(51) Int. Cl.
*A61B 17/02*    (2006.01)

(52) U.S. Cl. ...................................... 606/96
(58) Field of Classification Search .............. 606/79, 606/80, 86, 96–98
See application file for complete search history.

(56) References Cited

U.S. PATENT DOCUMENTS

| | | | |
|---|---|---|---|
| 125,642 | A | 4/1872 | Whitus |
| 169,075 | A | 10/1875 | Batson |
| 232,851 | A | 10/1880 | Rutter |
| 413,178 | A | 10/1889 | Doe |
| 2,483,060 | A | 9/1949 | Niedelman et al. |
| 2,833,168 | A | 5/1958 | Nelson |
| 3,216,288 | A | 11/1965 | Gardner |
| 3,574,290 | A | 4/1971 | Eckman |
| 3,583,822 | A | 6/1971 | Alexander et al. |
| 3,682,177 | A | 8/1972 | Ames et al. |
| 4,039,266 | A | 8/1977 | O'Connell |
| 4,072,440 | A | 2/1978 | Glover |
| 4,113,404 | A | 9/1978 | Lippacher et al. |
| 4,256,422 | A | 3/1981 | Theissig et al. |
| 4,281,949 | A | 8/1981 | Bugarin |
| 4,341,206 | A | 7/1982 | Perrett et al. |
| 4,354,779 | A | 10/1982 | Vaughan |
| 4,521,145 | A | 6/1985 | Bieler |
| 4,538,943 | A | 9/1985 | Clifton et al. |
| 4,546,859 | A | 10/1985 | Newman |
| 4,588,334 | A | 5/1986 | Khurana |

(Continued)

FOREIGN PATENT DOCUMENTS

CH        666207 A5    7/1988

(Continued)

*Primary Examiner*—Eduardo Robert
*Assistant Examiner*—Mary Hoffman
(74) *Attorney, Agent, or Firm*—Jones Day (57) ABSTRACT

The present invention is directed to a surgical drill guide. The drill guide may include a first drill guide body having a distal end for placement substantially adjacent a bone, a second drill guide body slidable with respect to the first drill guide body and having a proximal end for contacting a portion of a drill bit, a handle associated with at least one of the first drill guide body and the second drill guide body, and a detent mechanism for releasably retaining the position of the first drill guide body with respect to the second drill guide body in predefined increments. Additionally or alternatively, the drill guide may include a locking member movable between a first position where it substantially prevents sliding of the second drill guide body with respect to the first drill guide body, and a second position where it permits sliding of the second drill guide body with respect to the first drill guide body. The locking member may be resiliently biased to the first position. Other features for improving the drill guide are disclosed and claimed as well.

26 Claims, 8 Drawing Sheets

U.S. PATENT DOCUMENTS

| | | |
|---|---|---|
| 4,591,299 A | 5/1986 | Eckman |
| 4,592,257 A | 6/1986 | Durr |
| 4,592,681 A | 6/1986 | Pennison et al. |
| 4,647,260 A | 3/1987 | O'Hara et al |
| 4,668,134 A | 5/1987 | Vindez |
| 4,674,927 A | 6/1987 | Khurana |
| 4,681,490 A | 7/1987 | Pennison et al. |
| 4,708,139 A | 11/1987 | Dunbar |
| 4,710,075 A | 12/1987 | Davison |
| 4,714,469 A | 12/1987 | Kenna |
| 4,739,751 A | 4/1988 | Sapega et al. |
| 4,920,958 A | 5/1990 | Walt et al. |
| 4,922,897 A | 5/1990 | Sapega et al. |
| 5,026,376 A | 6/1991 | Greenberg |
| 5,054,968 A | 10/1991 | Eckman |
| 5,071,293 A | 12/1991 | Wells |
| 5,112,337 A | 5/1992 | Paulos et al. |
| 5,133,720 A | 7/1992 | Greenberg |
| 5,154,720 A | 10/1992 | Trott et al. |
| 5,163,940 A | 11/1992 | Bourque |
| 5,180,388 A | 1/1993 | DiCarlo |
| 5,330,468 A | 7/1994 | Burkhart |
| 5,350,380 A | 9/1994 | Goble et al. |
| 5,350,383 A | 9/1994 | Schmieding et al. |
| 5,354,300 A | 10/1994 | Goble et al. |
| 5,380,132 A | 1/1995 | Parks |
| 5,382,120 A | 1/1995 | Parsons |
| 5,409,493 A | 4/1995 | Greenberg |
| D359,557 S | 6/1995 | Hayes |
| 5,458,602 A | 10/1995 | Goble et al. |
| 5,562,664 A | 10/1996 | Durlacher et al. |
| 5,601,387 A | 2/1997 | Sanford et al. |
| 5,613,971 A | 3/1997 | Lower et al. |
| 5,681,333 A | 10/1997 | Burkhart et al. |
| 5,743,916 A | 4/1998 | Greenberg et al. |
| 5,746,552 A | 5/1998 | Tsui et al. |
| 5,810,826 A | 9/1998 | .ANG.kerfeldt et al. |
| 5,810,828 A | 9/1998 | Lightman et al. |
| 5,829,931 A | 11/1998 | Doumani |
| 5,888,034 A | 3/1999 | Greenberg |
| 5,891,150 A | 4/1999 | Chan |
| 5,895,389 A | 4/1999 | Schenk et al. |
| 5,941,884 A | 8/1999 | Corvelli et al. |
| 5,968,050 A | 10/1999 | Torrie |
| 6,019,767 A | 2/2000 | Howell |
| 6,110,178 A | 8/2000 | Zech et al. |
| 6,120,511 A | 9/2000 | Chan |
| 6,162,226 A | 12/2000 | DeCarlo et al. |
| 6,187,011 B1 | 2/2001 | Torrie |
| 6,210,415 B1 | 4/2001 | Bester |
| 6,213,770 B1 | 4/2001 | Kuhn |
| 6,342,057 B1 | 1/2002 | Brace et al. |
| 6,375,658 B1 | 4/2002 | Hangody et al. |
| 6,379,364 B1 | 4/2002 | Brace et al. |
| 6,436,103 B1 | 8/2002 | Suddaby |
| 6,443,676 B1 | 9/2002 | Kopras |
| 6,447,221 B1 | 9/2002 | Chen |
| 6,499,221 B1 | 12/2002 | Kuhn et al. |
| 6,514,258 B1 | 2/2003 | Brown et al. |
| 6,520,509 B1 | 2/2003 | Vasudeva et al. |
| 2002/0122706 A1 | 9/2002 | Chen |
| 2003/0000347 A1 | 1/2003 | Kriaski et al. |
| 2003/0051591 A1 | 3/2003 | Gobel et al. |
| 2003/0233098 A1 * | 12/2003 | Markworth ............ 606/96 |

FOREIGN PATENT DOCUMENTS

| | | |
|---|---|---|
| DE | 3800482 A1 | 7/1989 |
| EP | 261386 A2 | 3/1988 |
| GB | 2014884 A | 9/1979 |
| GB | 2288757 A | 11/1995 |
| JP | 62188612 A | 8/1987 |
| JP | 63267107 A | 11/1988 |
| JP | 5245162 A | 9/1993 |
| JP | 5277129 A | 10/1993 |
| WO | WO 99/29237 A1 | 6/1999 |
| WO | WO 0158630 A1 | 8/2001 |
| WO | WO 02/067786 A1 * | 9/2002 |

* cited by examiner

SURGICAL DRILL GUIDE

TECHNICAL FIELD OF THE INVENTION

The present invention relates generally to surgical drill guides. More specifically, the present invention relates to surgical drill guides for positioning, orienting and measuring the depth of holes to be drilled in bone tissue.

BACKGROUND OF THE INVENTION

It is well known to drill holes in bones in order to accommodate fastening devices used to anchor implants within a patient's body. For instance, pedicle screws have been used to anchor instrumentation systems to the spinal column of patients for correcting a variety of spinal disorders. One commonly used technique for inserting a pedicle screw into the bone includes the preparation of a pilot hole through the pedicle before inserting the screw therein. Typically, the selection of the insertion point is made based on the anatomy of the vertebra. Once the insertion point has been selected, a drill guide may be used to guide the drill bit along the proper axis, and/or to set the depth to which the drill bit penetrates the bone. Conventional drill guides generally include a handle having an adjustable length sleeve attached thereto. When used in conjunction with a drill bit having a fixed stop, the length of the sleeve may control the depth to which the drill penetrates the bone (and the depth of the consequent hole). Known drill guides, however, may include one or more drawbacks. For example, it may be necessary to rotate or screw an inner sleeve within an outer sleeve (or other member) to adjust the hole depth. This process can be timely, and may require removing the drill guide from the incision in order to make subsequent adjustments. Known drill guides may also lack any type of incremental adjustment of the hole depth, which may also add to the time required for the adjustment process. In addition, with known drill guides, one or more parts necessary to adjust the hole depth may be located in the patient, thus requiring the drill guide to be removed from the incision in order to adjust the hole depth. Further, known drill guides are often complicated to adjust. Thus, there remains a need in the art for surgical drill guides that provide quick and easy adjustment of the hole depth, allow for such adjustment from outside of the patient, can be left in place during adjustment of the hole depth, and are ergonomic, aesthetically pleasing, and easy to use.

SUMMARY OF THE INVENTION

The present invention is directed to a surgical drill guide. The drill guide may include a first drill guide body having a distal end for placement substantially adjacent a bone, a second drill guide body slidable with respect to the first drill guide body and having a proximal end for contacting a portion of a drill bit, a handle associated with at least one of the first drill guide body and the second drill guide body, and a detent mechanism for releasably retaining the position of the first drill guide body with respect to the second drill guide body in predefined increments. The proximal end may be spaced a first distance from the distal end, and the detent mechanism may provide incremental adjustment of the first distance. The first distance may determine the maximum penetration depth of a drill bit inserted through the first drill guide body and the second drill guide body.

The detent mechanism may comprise a detent body that engages the first drill guide body or the second drill guide body. For example, the detent body may be resiliently biased toward the first drill guide body or the second drill guide body, such as by a spring. The detent body may engage a plurality of detents defined on the second drill guide body. For example, the detent body may include an angular tip that engages the detents. Additionally or alternatively, the detents may be angular indentations defined on the second drill guide body.

The surgical drill guide may further include a locking member movable between a first position where it substantially prevents adjustment of the second drill guide body with respect to the first drill guide body, and a second position where it permits adjustment of the second drill guide body with respect to the first drill guide body. For example, the locking member may be slidable or pivotable between the first position and the second position. The locking member may be resiliently biased toward the first position. The locking member may engage a portion of the detent mechanism when the locking member is in the first position. Alternatively, the locking member may engage the plurality of detents when in the first position.

The first drill guide body and the second drill guide body may define a common longitudinal axis. The second drill guide body may be slidable within the first drill guide body, or vice versa. The first drill guide body and/or the second drill guide body may comprise a substantially tubular shaft. The distal end of the first drill guide body may include at least two projections for engaging the bone. The proximal end of the second drill guide body may in operation engage a fixed stop on a drill bit. The proximal end of the second drill guide body may include an enlarged diameter head which may facilitate engagement with the fixed stop.

The handle may be connected to at least one of the first drill guide body and the second drill guide body. For example, the handle may be connected to the first drill guide body by a stem portion. The handle may be configured and dimensioned for grasping by a user's hand.

According to another embodiment of the invention, the surgical drill guide may include a first drill guide body having a distal end for placement substantially adjacent a bone, a second drill guide body slidable with respect to the first drill guide body and having a proximal end for contacting a portion of a drill bit, a handle associated with at least one of the first drill guide body and the second drill guide body, and a locking member movable between a first position where it substantially prevents sliding of the second drill guide body with respect to the first drill guide body, and a second position where it permits sliding of the second drill guide body with respect to the first drill guide body, wherein the locking member is resiliently biased to the first position. The locking member may engage a plurality of detents defined on the second drill guide body.

The drill guide may further include a detent mechanism for releasably retaining the position of the first drill guide body with respect to the second drill guide body in predefined increments, and the locking member may engage a portion of the detent mechanism when the locking member is in the first position. For example, the locking member may engage a detent body.

The locking member may be located between the handle and the first drill guide body and the second drill guide body. For example, the drill guide may include a stem portion extending between the handle and the first drill guide body, wherein the locking member is located on the stem portion, in which case the locking member may be slidable on the stem portion.

According to yet another embodiment of the invention, the drill guide may include a first drill guide body having a distal end for placement substantially adjacent a bone, a second drill guide body slidably disposed within the first drill guide body, the second drill guide body having a proximal end for contacting a portion of a drill bit, a handle associated with at least one of the first drill guide body and the second drill guide body, and a detent body slidable with respect to at least one of the first drill guide body and the second drill guide body, wherein at least one of the first drill guide body and the second drill guide body includes a plurality of detents and the detent body is resiliently biased into engagement with one or more of the plurality of detents. The detent body may be resiliently biased into engagement with one or more of the plurality of detents by a spring. The drill guide may include a stem portion extending between the handle and at least one of the first drill guide body and the second drill guide body, and the detent body may be slidable on the stem portion.

BRIEF DESCRIPTION OF THE DRAWINGS

The detailed description will be better understood in conjunction with the accompanying drawings, wherein like reference characters represent like elements, as follows.

DETAILED DESCRIPTION OF THE PREFERRED EMBODIMENTS

Figure 1:
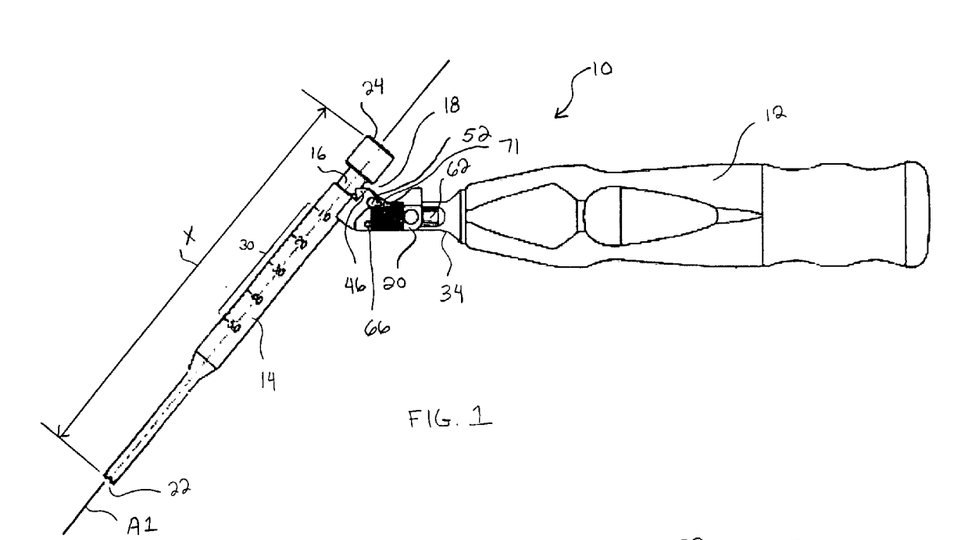
FIG. 1 is a side view of a first illustrative embodiment of a drill guide according to the present invention.
Figure 2:
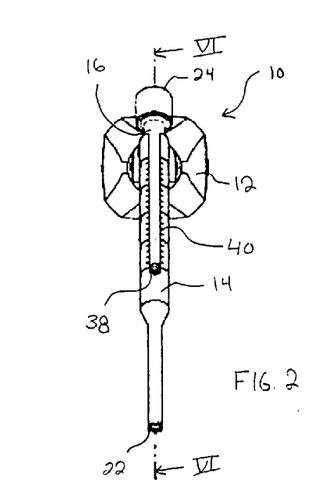
FIG. 2 is a front view of the drill guide of FIG. 1.

Referring to FIGS. 1 and 2, an illustrative embodiment of a surgical drill guide according to the present invention is shown. Drill guide 10 may generally include a handle 12, a first drill guide body 14, and a second drill guide body 16. Drill guide 10 may also include a detent mechanism 18 (such as shown in detail in FIG. 6) and/or a locking member 20. First drill guide body 14 and second drill guide body 16 may be substantially tubular shafts that slide or telescope with respect to one another. According to one preferred embodiment, second drill guide body 16 may slide within first drill guide body 14 along a common longitudinal axis A1, however other configurations are possible. When second drill guide body 16 is received within first drill guide body 14, the first and second drill guide bodies 14, 16 preferably define a common cannula for receiving a drill bit. By holding the drill guide 10 by its handle 12 and inserting a drill bit through the cannula, the user may control the insertion point and/or the orientation of the drill bit.

Figure 13:
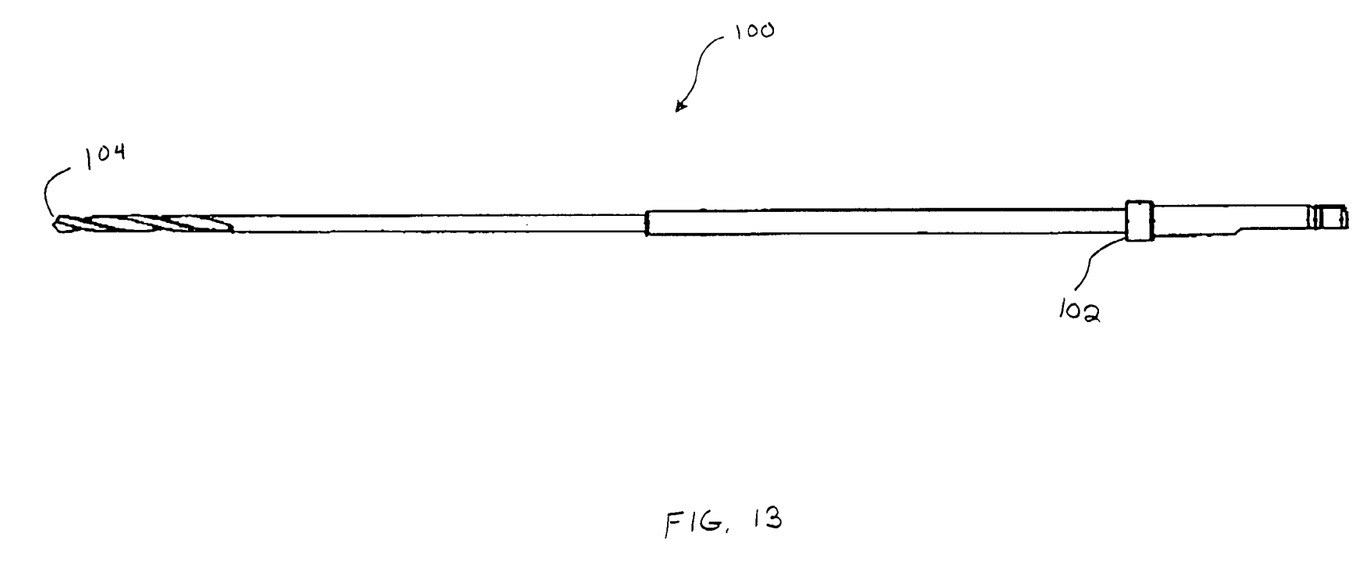
FIG. 13 is a side view of an illustrative embodiment of a drill bit having a fixed stop.

First drill guide body 14 may include a distal end 22 and second drill guide body 16 may include a proximal end 24. By sliding second drill guide body 16 with respect to first drill guide body 14, or vice versa, the distance X between distal end 22 and proximal end 24 may be adjusted. When used in conjunction with a drill bit having a known length (for example, the drill bit 100 shown in FIG. 13), the distance X between the distal end 22 and the proximal end 24 may be adjusted to set the maximum depth to which the drill bit penetrates the bone. For example, the distal end 22 of the first drill guide body 14 may be placed substantially adjacent the bone, and drill bit 100 may be inserted into the cannula in the first and second drill guide bodies 14, 16 and drilled into the bone until a fixed stop 102 (or other enlarged diameter portion) located a predetermined distance from the tip 104 of the drill bit contacts the proximal end 24 of the second drill guide body 16, at which point the first and second drill guide bodies 14, 16 prevent further penetration of the drill bit 100 into the bone. One of ordinary skill in the art will appreciate that drill bit 100 is shown for illustrative purposed only, and that drill guide 10 may be used with any drill bit known in the art, with or without a fixed stop.

Handle 12 may be shaped and dimensioned to fit comfortably in the user's hand and may be provided with knurling, grooves, ridges, bumps, serrations, or other known surface treatments to increase a user's grip thereon. Additionally or alternatively, handle 12 may have a rubber, silicone or other coating.

Figure 3:
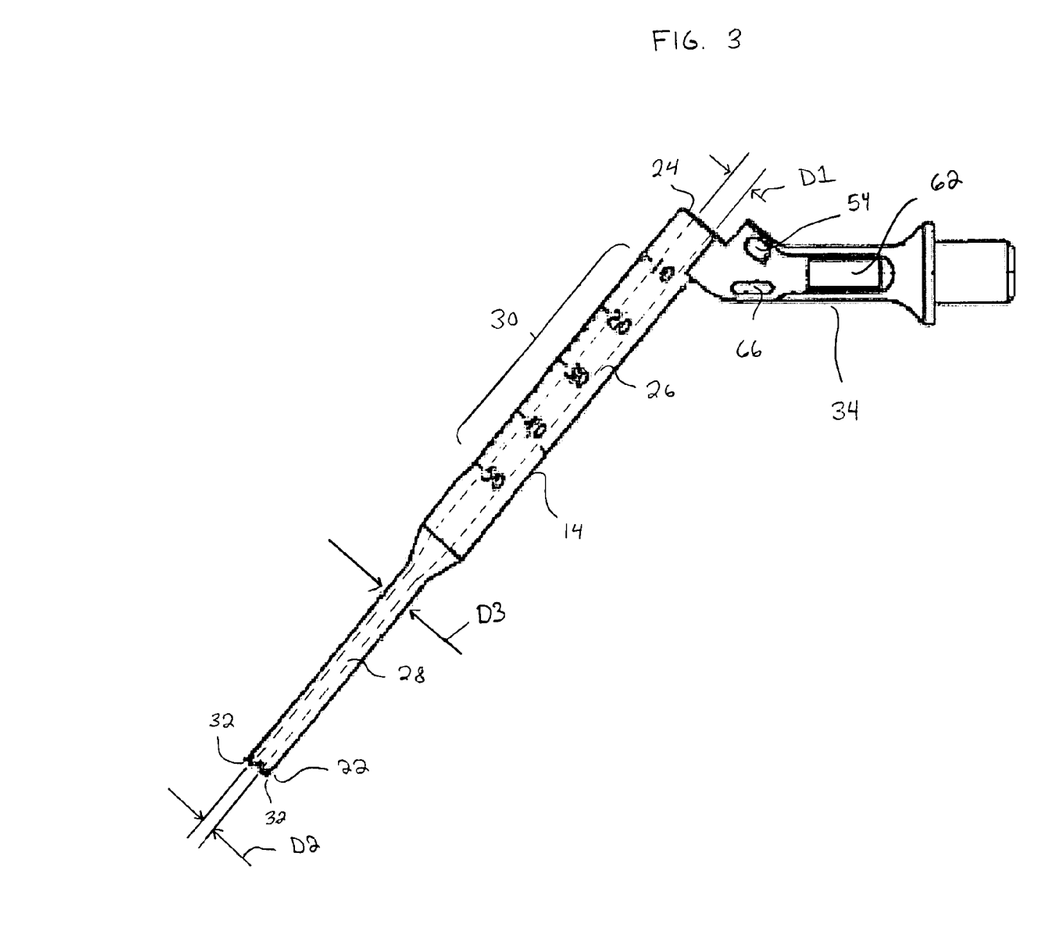
FIG. 3 is side view of a first drill guide body of the drill guide of FIG. 1.

As shown in FIG. 3, one illustrative embodiment of first drill guide body 14 may comprise a substantially tubular shaft, and may have an upper portion 26 and a lower portion 28. Upper portion 26 may have an inner diameter D1 that is configured and dimensioned to receive, and preferably slidably receive, second drill guide body 16. Lower portion 28 may have an inner diameter D2 that is smaller than inner diameter D1, but is sufficient to allow the drill bit to extend therethrough. Alternatively, the inner diameter D2 of lower portion 28 may also be configured and dimensioned to receive second drill guide body 16 (e.g., inner diameter D2 may be equal to or larger than D1). Lower portion 28 may also have a reduced outer diameter D3 in comparison to upper portion 26. The reduced outer diameter D3 may facilitate minimally invasive insertion of first drill guide body 14 into the patient; and may also aid in accessing difficult to reach areas. According to an alternative embodiment contemplated by the present invention, the first drill guide body 14 may be received within the second drill guide body 16.

Still referring to FIG. 3, a graduated scale 30 may be provided on first drill guide body 14, which may assist in determining the penetration depth of the drill bit, as will be discussed in more detail below. Alternatively, the graduated scale 30 may be provided on second drill guide body 16. Distal end 22 may have two or more projections 32 formed thereon that may engage the bone and stabilize the position of distal end 22. Projections 32 may have sharply pointed tips to ease penetration into the bone surface. A stem portion 34 may extend between first drill guide body 14 and handle 12, however first drill guide body 14 may alternatively be connected directly to handle 12. Handle 12 and stem portion 34 may be formed integrally, or as two separate points that are joined together. Preferably, stem portion 34 and first drill guide body 14 are formed integrally, however other configurations are possible. It is also contemplated that second drill guide body 16 may be connected to handle 12 in addition to, or instead of, first drill guide body 14, as will be understood by one of ordinary skill in the art from this disclosure.

Figure 4:
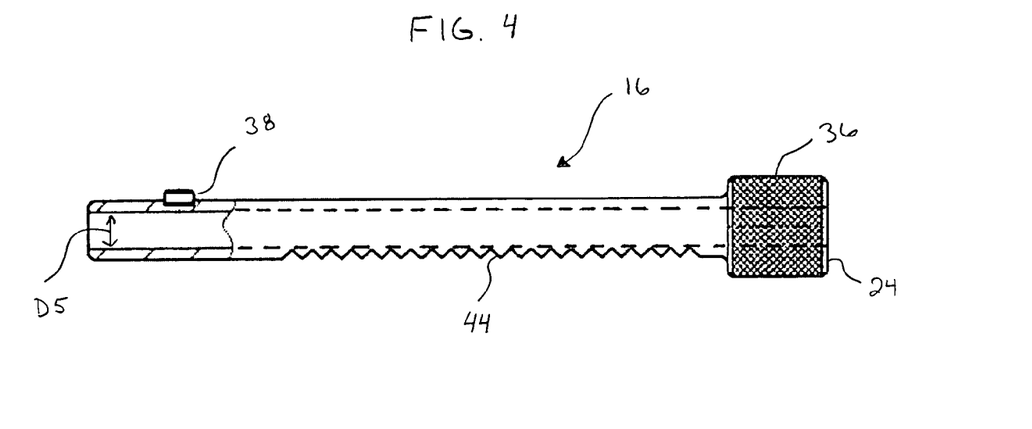
FIG. 4 is a side view of a second drill guide body of the drill guide of FIG. 1, with portions shown in cross-section.
Figure 5:
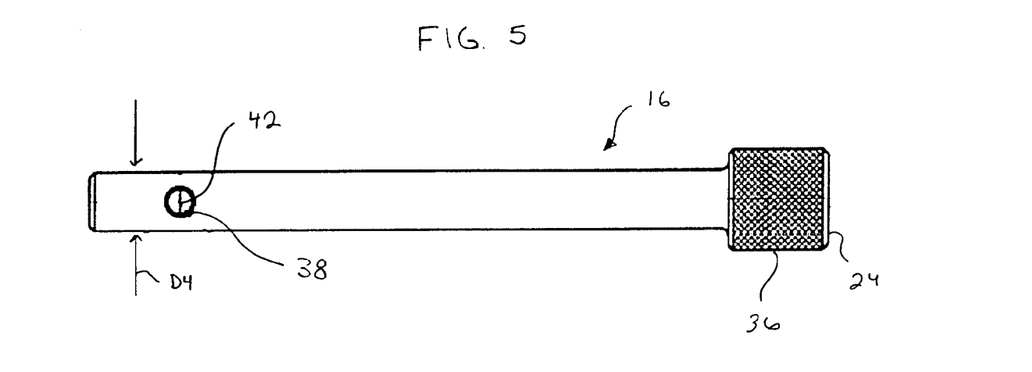
FIG. 5 is a top view of the second drill guide body of FIG. 4.

Referring to FIGS. 4 and 5, an illustrative embodiment of second drill guide body 16 is shown in detail. Second drill guide body 16 may comprise a substantially tubular shaft having an outer diameter D4 (shown in FIG. 4) that is dimensioned and configured for second drill guide body 16 to fit within first drill guide body 14. For example, outer diameter D4 may be slightly smaller than the inner diameter D1 of first drill guide body 14, allowing second drill guide body 16 to slide or telescope within first drill guide body 14. Second drill guide body 16 may also have an inner diameter D5 (shown in FIG. 4) that is configured and dimensioned to receive the drill bit. Preferably, inner diameter D5 is substantially equal to the inner diameter D2 of the lower portion 28 of first drill guide body 14, however other configurations and dimensions are possible. Second drill guide body 16 may have an enlarged diameter head 36 at proximal end 24, which may serve to engage a fixed stop or other feature on the drill bit or drill.

Head 36 may also facilitate gripping by the user in order to, for example, slide or telescope second drill guide body 16 with respect to first drill guide body 14, or vice versa. Thus, head 36 may be provided with knurling, grooves, ridges, bumps, serrations, or other known surface treatments to increase a user's grip thereon. Alternatively, head 36 may have a rubber, silicone, or other coating. While not shown, it is contemplated that a lever or other mechanism may optionally be provided to cause second drill guide body 16 to slide or telescope with respect to first drill guide body 14. For example, drill guide 10 may include a lever or other mechanism that a user may operate with the hand holding handle 12 to adjust the distance between distal end 22 and proximal end 24, as will be appreciated by one of ordinary skill in the art.

Still referring to FIGS. 4 and 5, second drill guide body 16 may include a peg 38 configured and dimensioned to prevent rotation of second drill guide body 16 within first drill guide body 14. For example, peg 38 may fit within a track 40 defined in first drill guide body 14, such as shown in FIG. 2. Peg 38, or alternatively another part of second drill guide body 16, may include a marker 42 (such shown in FIG. 5) that works in conjunction with the graduated scale 30 on first drill guide body 14 to indicate the penetration depth of the drill bit (based, in part, on the distance X between proximal end 22 and distal end 24 and the length of the drill bit). Second drill guide body 16 may also include a plurality of detents 44, such as shown in FIG. 4. As shown, the detents 44 may comprise one or more angular or V-shaped indentations defined on second drill guide body 16, however other shapes and configurations are contemplated. For example, detents 44 may alternatively comprise one or more protrusions defined on second drill guide body 16. Also, other embodiments are contemplated where the detents 44 are associated with or defined on the first drill guide body 14. As will be explained in more detail below, detents 44 may form part of a detent mechanism for releasably retaining the position of the first drill guide body 14 with respect to the second drill guide body 16 in predetermined increments. Peg 38 may be oriented with respect to detents 44 in order to maintain detents 44 in proper alignment with other parts of the detent mechanism. As shown, detents 44 are diametrically opposite peg 38, however other orientations are contemplated.

Figure 6:
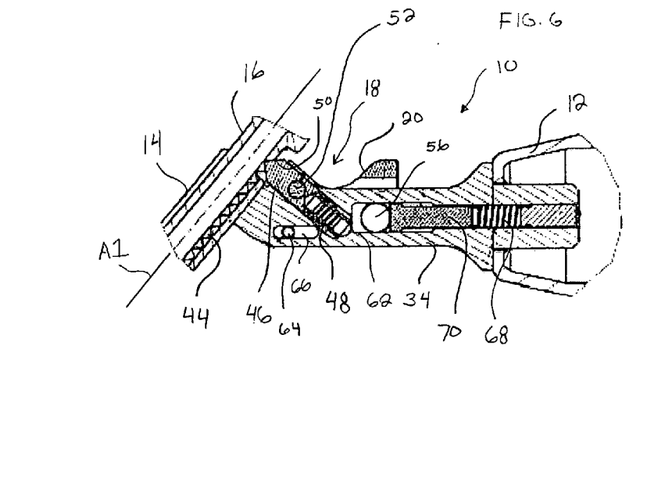
FIG. 6 is a cross-sectional view of a portion of the drill guide of FIG. 1, taken along line VI—VI of FIG. 2.

Referring to FIG. 6, one illustrative embodiment of a detent mechanism 18 is shown in cross-section. Detent mechanism 18 may operate to releasably retain the position of the first drill guide body 14 with respect to the second drill guide body 16 in predefined increments. Thus, a user may adjust the first distance X (shown in FIG. 1; defined between the distal end 22 of first drill guide body 14 and the proximal end 24 of second drill guide body 16) in predefined, known increments. When used in conjunction with a drill bit of a known length, this may permit incremental adjustment of the maximum penetration depth of the drill bit without the use of an external measuring device. This may also permit the user to adjust the maximum penetration depth of the drill bit without having to remove the drill guide 10 from the incision in the patient.

Graduated scale 30 may be calibrated for use with a drill bit having a predetermined length. For example, by subtracting the first distance X (between proximal end 24 and distal end 22) from the length of the drill bit, the exposed length of the drill bit may be determined. Using this convention, graduated scale 30 may be provided with markings indicating predefined maximum drill penetration depths (e.g., between 10 mm and 50 mm in 2 mm increments, or between 10 mm and 60 mm in 2 mm increments). Accordingly, graduated scale 30 and marker 42 (located on peg 38) may be read by the user to determine the maximum drill penetration depth. This may, among other things, allow the user to measure the maximum penetration depth without the use of extra measuring devices, and/or may allow the user to change the maximum penetration depth while the drill guide is still positioned inside the incision.

The detent mechanism 18 may comprise a detent body 46 (shown in detail in FIG. 7) capable of engagement with one or more detents 44 formed on the first drill guide body 14 or the second drill guide body 16. According to the illustrative embodiment shown, detent body 46 may be slidably mounted in a bore in stem 34, however other configurations are possible. For example, detent body 46 may alternatively be mounted in or on the handle 12, the first drill guide body 14, the second drill guide body 16, or any combination of these items. Detent body 46 may be resiliently biased into engagement with detents 44, such as by a first coil spring 48 or other known resilient member.

Interaction between detent body 46 and detents 44 preferably releasably retains the position of the first drill guide body 14 with respect to the second drill guide body 16 unless a sufficient force is applied to the drill guide bodies 14, 16 to change their relative positions. For example, in order to slide or telescope the second drill guide body 16 with respect to first drill guide body 14, a user may be required to impart sufficient force to the second drill guide body 16 (substantially along the first axis A1) in order to cause detent body 46 to move backwards against the first spring 48 sufficiently to disengage from the detent 44 and move into engagement with the adjacent detent 44. As shown in FIG. 6, detent body 46 may include an angular tip 50 and/or detents 44 may have corresponding angular shapes that act as ramps to cause detent body 46 to move away from second drill guide body 16 upon sliding of the second drill guide body 16 with respect to the first drill guide body 14 along first axis A1. Adjacent detents 44 may be spaced apart to provide the appropriate sized increments of the maximum drill bit penetration depth. Detents 44 may also extend over a sufficient distance to provide an appropriate range of adjustment of the maximum penetration depth. For example, according to one illustrative embodiment, adjacent detents 44 may be dimensioned and configured to provide depth adjustment from 10 mm to 50 mm in 2 mm increments.

Figure 7:
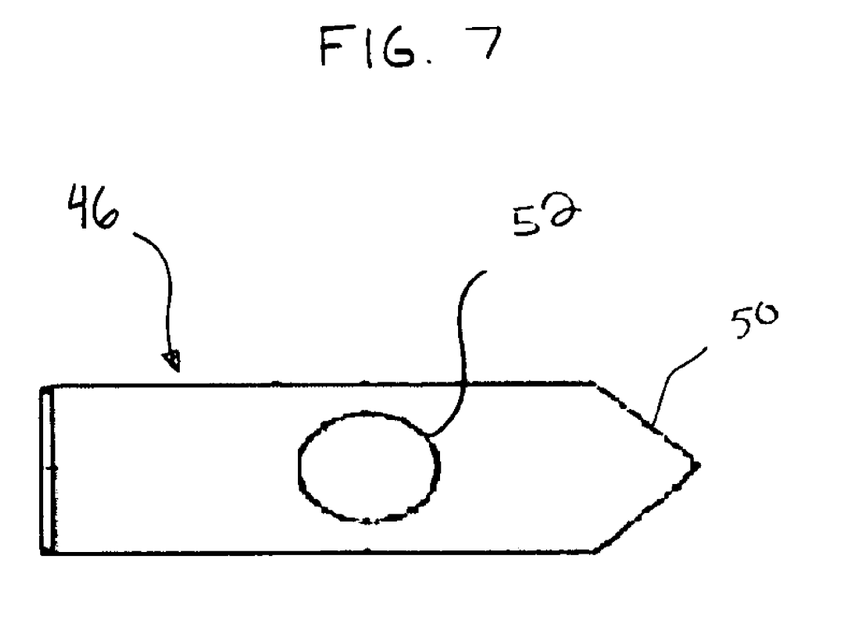
FIG. 7 is a side view of a detent body of the drill guide of FIG. 1.

Referring to FIGS. 6 and 7, detent body 46 may also include a first pin 52 or other member extending transversely therethrough. First pin 52 may slide in a first elongated slot 54 (shown in FIG. 3) provided in stem 34 or other part of drill guide 10. Interaction between first pin 52 and first slot 54 may captivate detent body 46 on drill guide 10, even if second drill guide body 16 is completely removed from the first drill guide body 14. This may be beneficial, for example, to permit ultrasonic, steam or autoclave cleaning of the second drill guide body 16. Other configurations and structures for captivating detent body 46 on drill guide 10 are contemplated by the present invention, as will be readily understood by one of ordinary skill in the art from this disclosure.

Referring now to FIGS. 1 and 6, drill guide 10 may additionally or alternatively include a locking member capable of substantially preventing sliding of second drill guide body 16 with respect to first drill guide body 14. For example, locking member 20 (shown in detail in FIGS. 8 and 9) may be normally located in a first position (shown in FIGS. 1 and 6) in which second drill guide body 16 is substantially prevented from sliding with respect to first drill guide body 14 (or vice versa) unless a user actively moves the locking member 20 to a second position (not shown), for example, toward handle 12 in FIGS. 1 and 6. This feature may, among other things, help prevent the first and second drill guide bodies 14, 16 from inadvertently moving or sliding with respect to one another during the drilling process.

Figure 8:
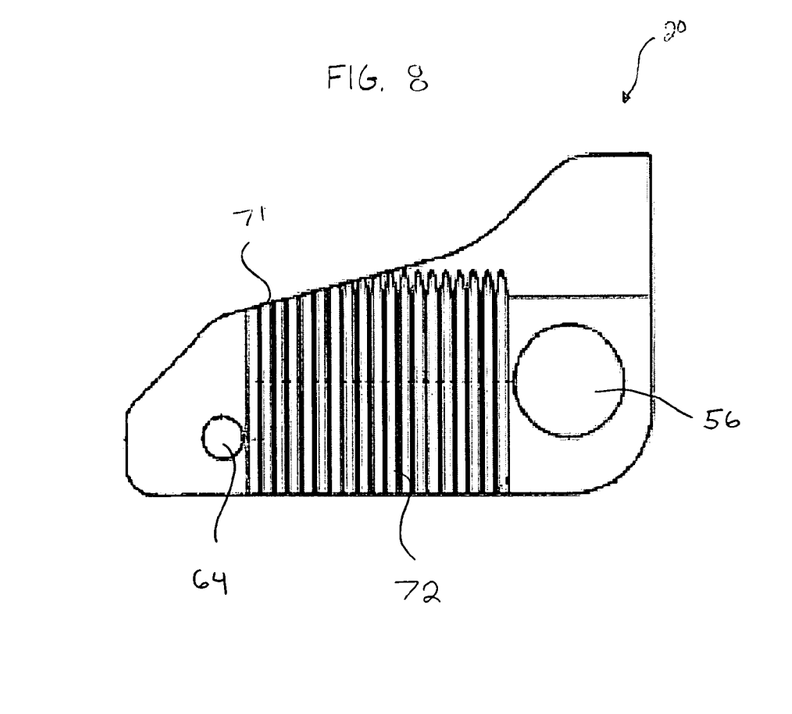
FIG. 8 is side view of a locking member of the drill guide of FIG. 1.
Figure 9:
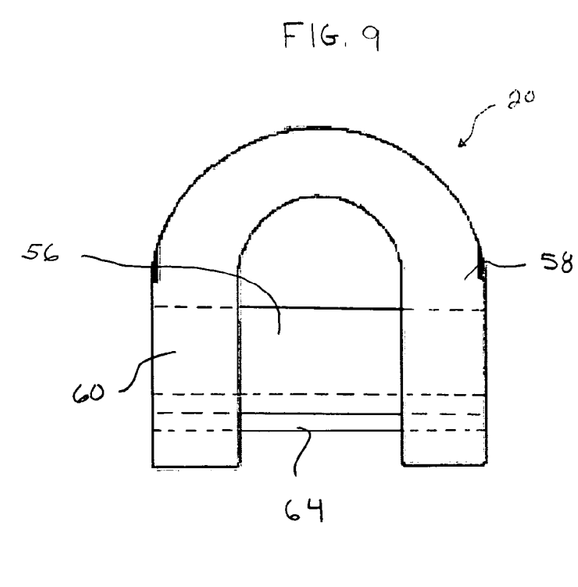
FIG. 9 is a back view of the locking member of FIG. 8.
Figure 10:
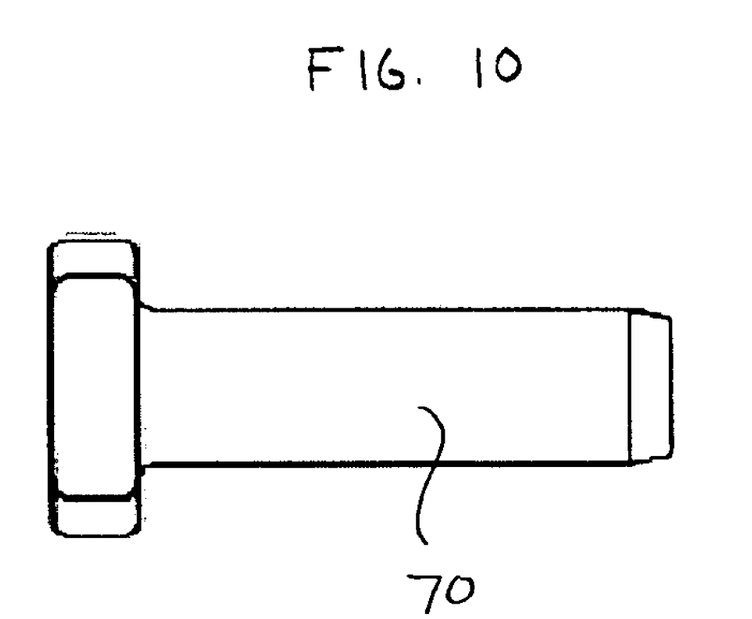
FIG. 10 is a side view of a plunger member of the drill guide of FIG. 1.

As shown in FIGS. 1 and 6, locking member 20 may be located on stem portion 34. According to the illustrative embodiment shown, locking member may have a substantially U-shaped cross-section (as shown in FIG. 9) that fits over stem portion 34, however other shapes and configurations are possible. A second pin 56 (shown in FIGS. 8 and 9) may extend between the sides 58, 60 of locking member 20 and through a second elongated slot 62 in stem portion 34. Additionally or alternatively, a third pin 64 (shown in FIGS. 8 and 9) may extend between the sides 58, 60 of locking member 20 and through a third elongated slot 66 in stem portion 34. The second and/or third pins 56, 64 may serve to secure locking member 20 on stem portion 34 so that locking member 20 can slide along stem portion 34 generally toward or away from the first and second body members 14, 16 (e.g., between the first and second positions). Locking member 20 may be biased towards the first position by, for example, a second coil spring 68 or other resilient member. In the illustrative embodiment shown, coil spring 68 may be located in second elongated slot 62 and press a plunger member 70 (also located in second elongated slot 62; shown in detail in FIG. 10) against second pin 56 to bias locking member 20 toward the first position, however, other configurations are contemplated.

When locking member 20 is in the first position, such as shown in FIGS. 1 and 6, a portion of locking member 20 may engage detent body 46 and prevent detent body 46 from moving sufficiently to disengage the detents 44 and allow the second drill guide body 16 to move or slide with respect to the first drill guide body 14. For example, locking member 20 may have one or more blocking surfaces 71 that contact or engage first pin 52 (or other part of the detent mechanism 18 or detent body 46) when locking member 20 is in the first position. Blocking surfaces 71 are preferably angled with respect to detent body 46 such that the forces applied by detent body 46 on blocking surfaces 71 (when detent body 46 is moved or attempted to be moved out of engagement with detents 44) results in little or no forces tending to move locking member 20 from the first position toward the second position (i.e., a low pressure angle). When locking member 20 is moved to the second position by the user (e.g., sufficiently towards handle 12 in FIGS. 1 and 6), the blocking surfaces 71 move sufficiently far out of contact with first pin 52 to allow detent body 46 to move far enough out of engagement with the detents 44 such that the first and second drill guide bodies 14, 16 can incrementally slide or telescope with respect to one another.

Figure 11:
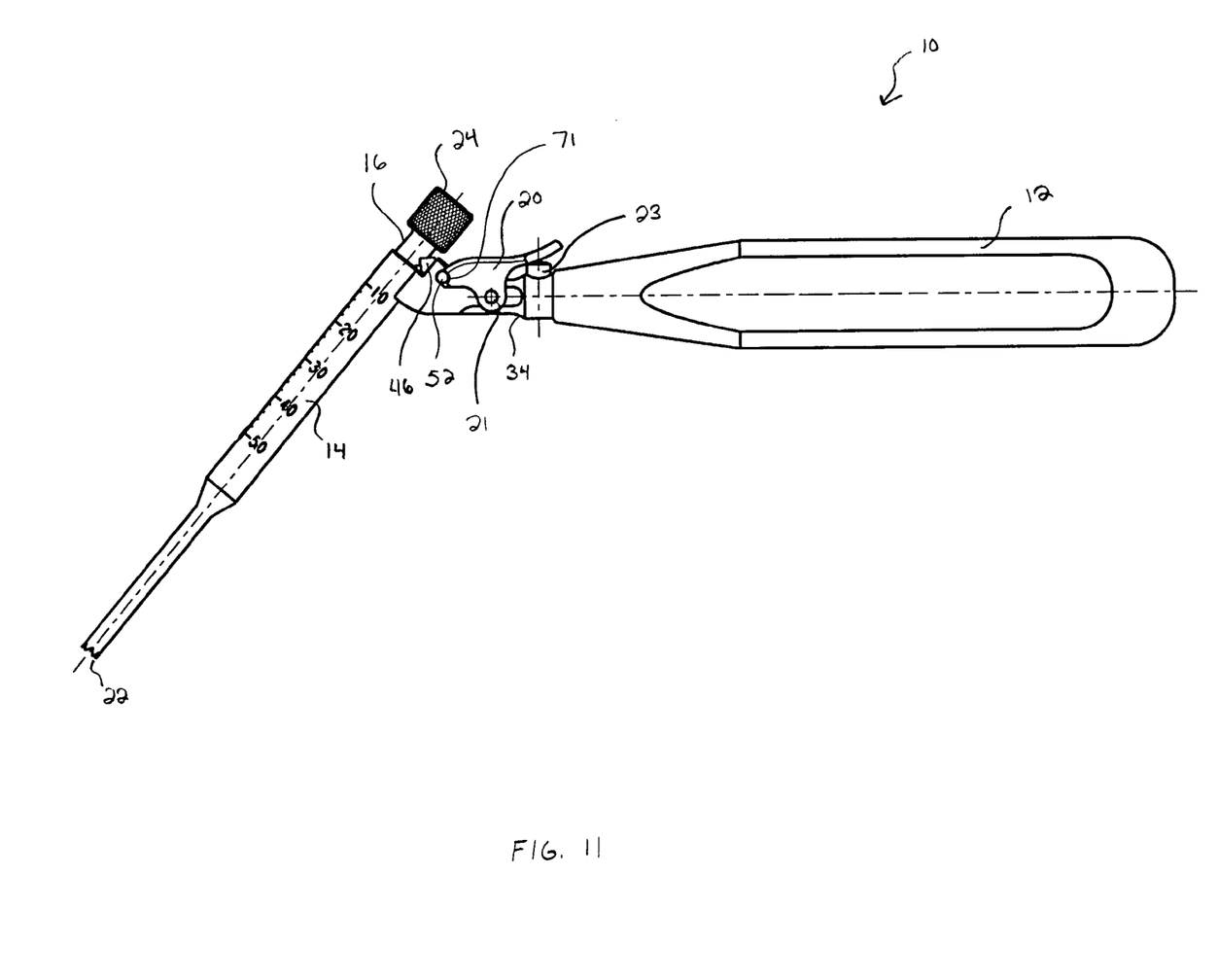
FIG. 11 is a side view of an alternative embodiment of the drill guide of FIG. 1.

As shown in FIG. 11, locking member 20 may alternatively pivot between the first position and the second position. For example, locking member 20 may pivot about a pivot pin 21 that extends through stem portion 34. A spring biased plunger 23 or other member may bias locking member 20 into the first position (shown), in which blocking surfaces 71 engage first pin 52, to prevent detent body 46 from moving sufficiently to allow the second drill guide body 16 to move or slide with respect to the first drill guide body 14. The locking member 20 may be pivoted about pivot pin 21 to the second position (against the force of the spring biased plunger 23) in which position the blocking surfaces 71 are a sufficient distance from first pin 52 to allow detent body 46 to move far enough out of engagement with the detents 44 such that the first and second drill guide bodies 14, 16 can incrementally slide or telescope with respect to one another.

Figure 12:
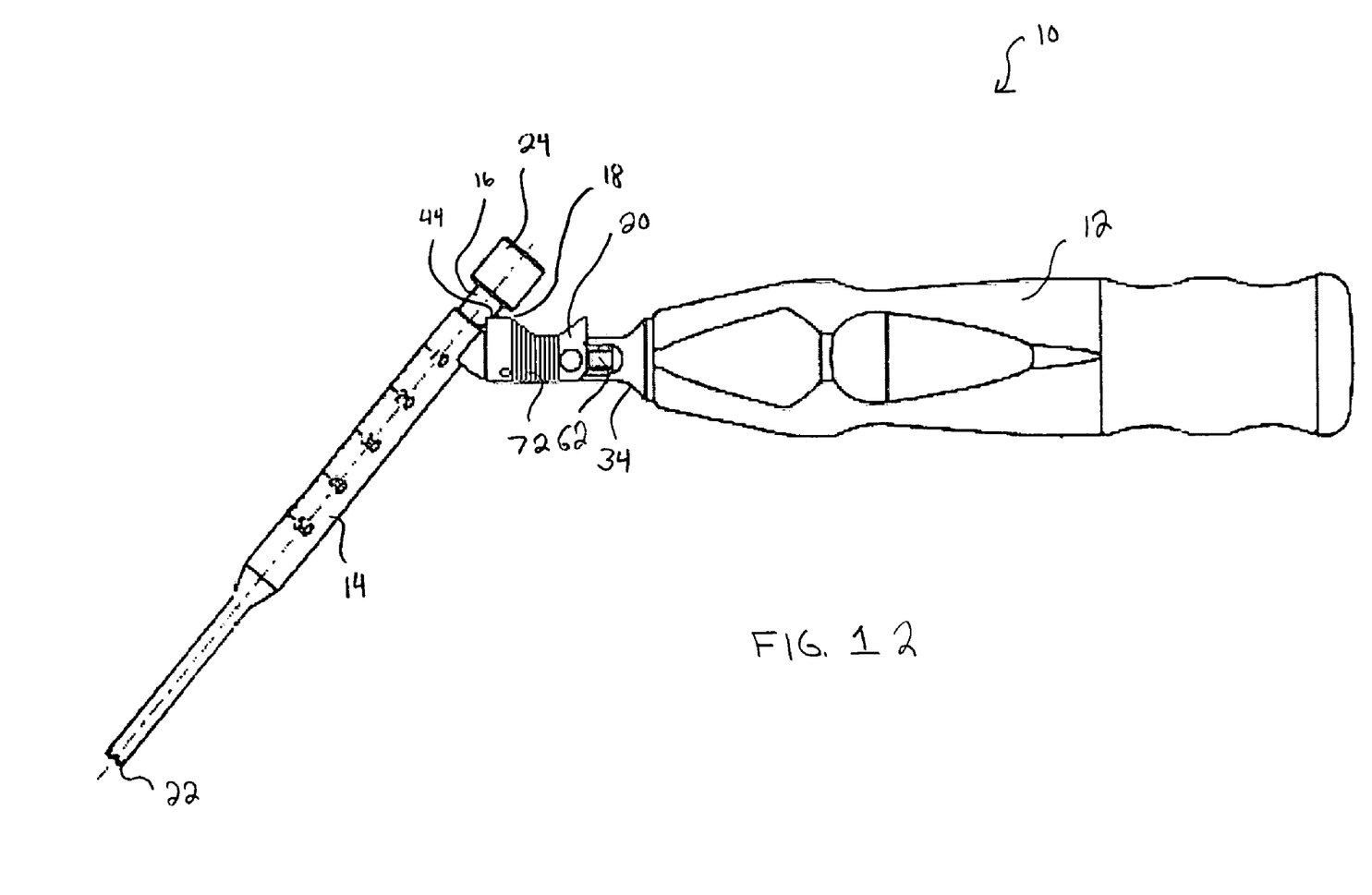
FIG. 12 is a side view of another alternative embodiment of the drill guide of FIG. 1.

As shown in FIG. 12, locking member 20 may alternatively engage the detents 44 themselves when locking member 20 is in the first position, thereby substantially preventing movement or sliding of the first drill guide body 14 with respect to the second drill guide body 16, or vice versa.

The locking member 20 is preferably configured and positioned so that it can be moved between the first and second positions by the thumb or finger of a hand holding the handle 12, however other configurations and positions are contemplated. As shown in FIG. 8, locking member 20 may be provided with ridges 72 or other known surface treatments to increase a user's grip thereon, such as knurling, grooves, bumps, or serrations. Additionally or alternatively, locking member 20 may have a rubber, silicone, or other coating. Although locking member 20 is shown and described as slidably mounted to stem portion 34, other configurations and locations are contemplated. For example, locking member 20 may alternatively or additionally be mounted in, on, or associated with handle 12, first drill guide body 14, second drill guide body 16, and/or some other part of drill guide 10.

Drill guide 10 may be used to position, orient and/or measure the depth of holes to be drilled in bone tissue, such as, for example, a vertebra. By positioning distal end 22 against the vertebra and inserting a drill bit through the first and second drill guide bodies 14, 16, drill guide 10 may be used to control the starting point of the hole to be drilled, and/or the angular orientation of the hole. Alternatively or additionally, drill guide 10 may be used to measure the depth of the hole. For example, when used in conjunction with a drill bit having a fixed stop or similar feature, the distance between the distal end 22 and the proximal end 24 may be adjusted to determine the maximum penetration depth of the drill bit (assuming, for example, that the drill bit is inserted into the first and second drill guide bodies 14, 16 until the fixed stop or other feature engages or contacts proximal end 24). Detent mechanism 18 may provide incremental adjustment of the maximum penetration depth, as explained above. Also, locking member 20 may prevent accidental or inadvertent adjustment of the distance between the distal end 22 and proximal end 24 during drilling or other operations. Also, due to the configuration drill guide 10, a user may incrementally adjust the maximum penetration depth to a known value without the necessity of moving drill guide 10 away from the drilling site. One of ordinary skill in the art will appreciate that drill guide 10 may be used with other bone tissue besides the vertebrae, such as, for example, long bones.

While it is apparent that the illustrative embodiments of the invention herein disclosed fulfill the objectives stated above, it will be appreciated that numerous modifications and other embodiments may be devised by those skilled in the art. For example, the first drill guide body may alternatively slide or telescope within the second drill guide body; or the detent body may alternatively engage or contact the first drill guide body 14 or other portion of the drill guide. Therefore, it will be understood that the appended claims are intended to cover all such modifications and embodiments which come within the spirit and scope of the present invention.

What is claimed:

1. A surgical drill guide comprising:
   a first drill guide body having a distal end for placement substantially adjacent a bone, and a proximal end;
   a second drill guide body slidable with respect to the first drill guide body, the second drill guide body having a proximal end for contacting a portion of a drill bit;
   a handle associated with at least one of the first drill guide body and the second drill guide body; and
   a detent mechanism for releasably retaining the position of the first drill guide body with respect to the second drill guide body in predefined increments;
   wherein the detent mechanism engages the second drill guide body at a location outside of the first drill guide body and between the proximal end of the first drill guide body and the proximal end of the second drill guide body.

2. The surgical drill guide of claim 1, wherein the proximal end of the second drill guide body is spaced a first distance from the distal end of the first drill guide body, and the detent mechanism provides incremental adjustment of the first distance.

3. The surgical drill guide of claim 2, wherein the first distance determines a maximum penetration depth of a drill bit inserted through the first drill guide body and the second drill guide body.

4. The surgical drill guide of claim 1, wherein the detent mechanism comprises a detent body that engages the first drill guide body or the second drill guide body.

5. The surgical drill guide of claim 4, wherein the detent body is resiliently biased toward the first drill guide body or the second drill guide body.

6. The surgical drill guide of claim 5, further comprising a spring that biases the detent body toward the first drill guide body or the second drill guide body.

7. The surgical drill guide of claim 4, further comprising a stem portion connecting the handle to the first drill guide body or the second drill guide body, wherein the detent body is located in a cavity in the stem portion.

8. The surgical drill guide of claim 4, wherein the detent body engages a plurality of detents defined on the second drill guide body.

9. The surgical drill guide of claim 8, wherein the detent body includes an angular tip that engages the detents.

10. The surgical drill guide of claim 8, wherein the detents are angular indentations defined on the second drill guide body.

11. The surgical drill guide of claim 1, further comprising a locking member movable between a first position where it substantially prevents adjustment of the second drill guide body with respect to the first drill guide body, and a second position where it permits adjustment of the second drill guide body with respect to the first drill guide body.

12. The surgical drill guide of claim 11, wherein the locking member is slidable between the first position and the second position.

13. The surgical drill guide of claim 11, wherein the locking member is resiliently biased toward the first position.

14. The surgical drill guide of claim 13, further comprising a spring that biases the locking member toward the first position.

15. The surgical drill guide of claim 14, further comprising a plunger member disposed between the spring and the locking member.

16. The surgical drill guide of claim 15, further comprising a stem portion connecting the handle to the first drill guide body or the second drill guide body, wherein the spring and plunger member are located in a cavity in the stem portion.

17. The surgical drill guide of claim 11, wherein the locking member engages a portion of the detent mechanism when the locking member is in the first position.

18. The surgical drill guide of claim 1, wherein the first drill guide body and the second drill guide body define a common longitudinal axis.

19. The surgical drill guide of claim 1, wherein the second drill guide body is slidable within the first drill guide body.

20. The surgical drill guide of claim 1, wherein the first drill guide body is a substantially tubular shaft.

21. The surgical drill guide of claim 1, wherein the second drill guide body is a substantially tubular shaft.

22. The surgical drill guide of claim 1, wherein the distal end of the first drill guide body includes at least two projections for engaging the bone.

23. The surgical drill guide of claim 1, wherein the proximal end of the second drill guide body includes an enlarged diameter head for engaging a fixed stop on a drill bit.

24. The surgical drill guide of claim 1, wherein the handle is connected to at least one of the first drill guide body and the second drill guide body.

25. The surgical drill guide of claim 1, wherein the handle is connected to the first drill guide body by a stem portion.

26. The surgical drill guide of claim 1, wherein the handle is configured and dimensioned for grasping by a user's hand.

* * * * *